United States Patent
Brown

(10) Patent No.: US 6,692,449 B1
(45) Date of Patent: Feb. 17, 2004

(54) METHODS AND SYSTEM FOR ASSESSING LIMB POSITION SENSE DURING MOVEMENT

(75) Inventor: David A. Brown, Evanston, IL (US)

(73) Assignee: Northwestern University, Evanston, IL (US)

( * ) Notice: Subject to any disclaimer, the term of this patent is extended or adjusted under 35 U.S.C. 154(b) by 145 days.

(21) Appl. No.: 10/017,510

(22) Filed: Dec. 14, 2001

Related U.S. Application Data

(60) Provisional application No. 60/255,990, filed on Dec. 15, 2000.

(51) Int. Cl.[7] .......................... A61B 5/103; A61B 5/117
(52) U.S. Cl. ...................................................... 600/595
(58) Field of Search ................. 600/595, 587, 600/300; 482/57, 142, 51, 91, 63, 5, 62; 73/379.01, 379.02, 379.07; 601/32, 36, 40

(56) References Cited

U.S. PATENT DOCUMENTS

| | | | |
|---|---|---|---|
| 3,572,699 A | * 3/1971 | Nies ................................ 482/5 |
| 3,745,990 A | * 7/1973 | Neis ............................ 600/595 |
| 6,032,530 A | * 3/2000 | Hock ....................... 73/379.01 |

OTHER PUBLICATIONS

Brown, et al., Muscle activity adapts to anti–gravity posture during pedalling in persons with post–stroke hemiplegia, Brain, vol. 120, 1997, pp. 825–837, Oxford University Press 1997.

Brown, et al., Increased Workload Enhances Force Output During Pedaling Exercise in Persons With Poststroke Hemiplegia, Stroke, vol. 29, 1998, pp. 598–606, American Heart Association, Inc., 1998.

Kautz, et al., Relationships between timing of muscle excitation and impaired motor performance during cyclical lower extremity movement in post–stroke hemiplegia, Brain, vol. 121, 1998, pp. 515–526, Oxford University Press 1998.

Katchuk, et al., Limb Position Sense During Cyclic Movement, Conference Abstract, Neurology Report, Dec., 2000.

* cited by examiner

*Primary Examiner*—Max F. Hindenburg
*Assistant Examiner*—Brian Szmal
(74) *Attorney, Agent, or Firm*—Reinhart Boerner Van Deuren s.c.

(57) ABSTRACT

This invention includes methods and/or apparatus for limb position sensing and, more particularly, measurement of limb position acuity during an ongoing movement rather than after movement has stopped.

33 Claims, 5 Drawing Sheets

Target positions of the crank angle

| Crank Angle | Crank Angle Position | Position of foot |
|---|---|---|
| 0° | 1 | Closest to body |
| 30° | 2 | |
| 60° | 3 | |
| 90° | 4 | Midextension |
| 120° | 5 | |
| 150° | 6 | |
| 180° | 7 | Furthest from body |

Figure 3

INTRACLASS CORRELATION COEFFICIENT

| *Eyes/Condition* | *Error* |
|---|---|
| Open/Static | .97 |
| Open/Passive | .86 |
| Open/Active | .98 |
| Closed/Static | .92 |
| Closed/Passive | .95 |
| Closed/Active | .89 |

Figure 4

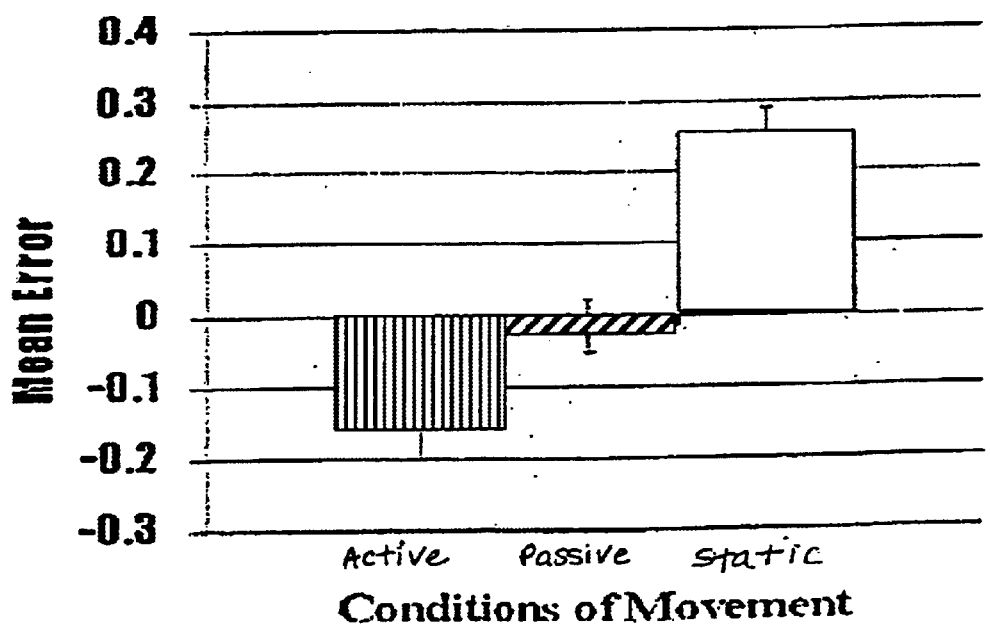
Figure 5. Movement Error Eyes Closed
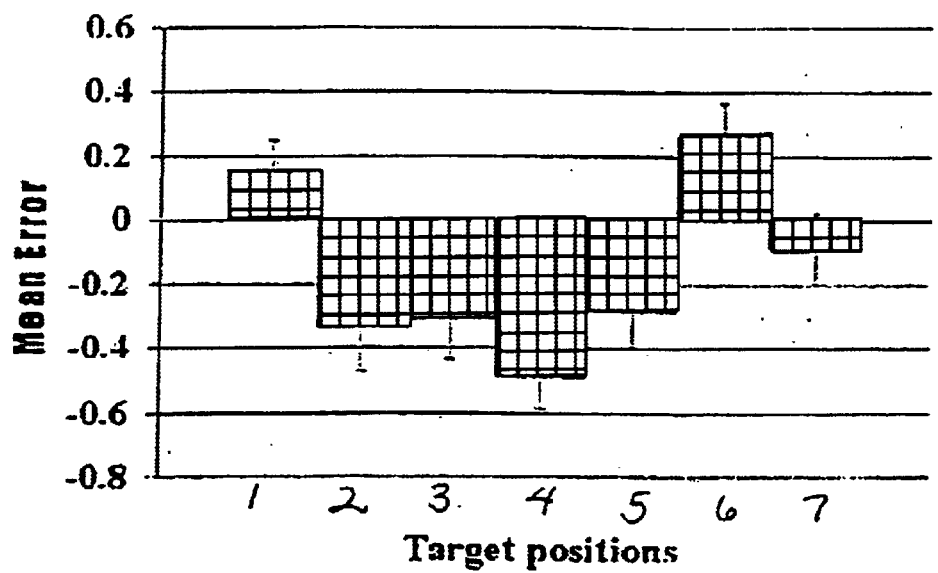
Figure 6. Intraphase error Active/Closed

METHODS AND SYSTEM FOR ASSESSING LIMB POSITION SENSE DURING MOVEMENT

This application claims priority benefit of U.S. Provisional Patent Application Serial No. 60/255,990, filed Dec. 15, 2000, the entirety of which is incorporated herein by reference.

BACKGROUND OF THE INVENTION

Limb position sense (LPS) is the ability to sense the movement and position of limbs in space. During locomotion, limb position sense is regulated by sensory feedback to the nervous system from proprioceptors, which include cutaneous, vestibular, muscle and joint receptors. Such proprioceptors respond to locomotion and provide the information needed to know the position of a subject's limb(s) in space. (Williams W J. A systems-oriented evaluation of the role of joint receptors and other afferents in position and motion sense. *CRC Critical Reviews in Biomedical Engineering.* 1981; 7:23–77.)

Proprioceptive feedback from muscle, joint and cutaneous receptors are essential for the generation of the normal motor pattern. (Gandevia S C, Burke D. Does the nervous system depend on kinesthetic information to control natural limb movements? *Behavioral and Brain Sciences.* 1992;15:614–632.) Neural stimulation detected by receptors travels to the central nervous system for integration via cortical and reflex pathways. These mechanoreceptors demonstrate adaptive properties depending on a particular stimulus. Pacinian corpuscles are quick adapting joint mechanoreceptors that decrease their discharge rate to extinction within milliseconds of the onset of a continuous stimulus. It is postulated that they mediate the sensation of joint motion because they are sensitive to changes in position. Slow-adapting mechanoreceptors, including muscle spindle, Golgi tendon organ and Ruffini ending joint receptors, are thought to mediate the sensation of joint position and changes in position because they are maximally stimulated at specific angles. (Lephart S M. Proprioception following ACL reconstruction. *J Sports Rehab.* 1992; 1:186–196.) Muscle spindle receptors are found within skeletal muscle and function to measure tension upon stretch of the muscle. Golgi tendon organs are located at the musculotendinous junction and function as a protective mechanism by inhibiting the motor neurons innervating the muscles that were stretched while exciting the motor nerves of the antagonistic muscles.

Various studies have also confirmed the role of these receptors in providing information to the central nervous system about tissue deformation. Other studies by Goodwin et al and Eklund showed that perception of limb position sense and movement is derived from muscle spindle. (Gandevia S C, Burke D. Does the nervous system depend on kinesthetic information to control natural limb movements? *Behavioral and Brain Sciences.* 1992; 15:614–632.) In their studies, when vibration was applied to muscles, tendon movement occurred. Direct recordings from human spindle afferents suggest that these movements depend upon signals from primary and secondary spindle endings. Hiebert et al indicated that proprioceptors that signal hip extension might arise from muscle spindle afferents. (Hiebert G W, Whelan P I, Prochazka A, Pearson K G. Contribution of hind limb flexor muscle afferents to the timing of phase transitions in the cat step cycle. *J Neurophysiol.* 1996; 75:1126–1137.) Gandevia and Burke, supra, demonstrated that acuity can be diminished with both cutaneous and joint anesthesia, particularly in joints in the hand.

Perception of afferent signals, however, is not required for movement. The spinal cord has complex neural circuitry, which is capable of producing rhythmic, oscillating commands to the musculature, even in the absence of sensory input. Central motor programs alone are sufficient to control simple learned movements. For example, Gandevia et al, supra, showed that subjects can recruit and grade the motor drive to a paralyzed muscle in the absence of feedback from that muscle. Grillner et al described research performed on animals (Grillner S. Locomotion in vertebrates: Central mechanisms and reflex interaction. *Physiol Reviews.* 1975; 55:247–304): The spinal cord of cats is cut at a level below the brain so that the higher centers cannot influence lower ones, and the cord is deafferented below the level of the cut. When the cord is stimulated, the cat produces stepping movements that resemble normal locomotion in cats without feedback from the limbs.

Afferent feedback, however, is critical in providing the central nervous system with input, especially when involving small, precise contractions during phase transitions or disturbances. Afferent signals, for example, are required to modulate the central pattern generator of the locust and thus for its nervous system to generate the appropriate motor pattern. When deafferented, the locust cannot maintain the normal flight rhythm despite a wind stimulus to its head. The authors explain that the change in flight behavior is associated with significant changes in the profile of synaptic activation in many interneurons in deafferented preparations and with alterations in the motor pattern.

Feedback during active and passive movements is more functional than during static positioning. Studies using microneurography of the human hand during active and passive movement show a response from cutaneous, joint and muscle afferents. During both active and passive movements, the majority of afferents from all classes of cutaneous receptors alter their discharge rates. In a static position, however, there is little background discharge in any of the cutaneous receptors. (Gandevia S C, Burke D. Ibid.)

In a review article spanning the past 20 years, Duysens and colleagues show the importance of proprioceptive feedback in triggering events in the gait cycle. (Duysens J, Clarac F, Cruse H. Load-regulating mechanisms in gait and posture: Comparative aspects. *Physiol Reviews.* 2000; 80:83–133.) They discuss research with spinal cats on a treadmill whereby they found that at end stance the cat's limb is extended and unloaded whereas at end swing the cat's limb is flexed and beginning to unload. Researchers then questioned what triggered these transitions. They postulated that the transition from stance to swing was triggered by load and the transition from flexion to extension was triggered by limb position sense.

Afferent feedback provides information about human movement and can influence normal movement. Sharma et al studied knee joints with and without osteoarthritis and identified two possible directions in the relationship between impaired proprioception and knee osteoarthritis: 1) that proprioceptive impairment contributes to the development of knee osteoarthritis; or 2) that knee position sense impairment results from osteoarthritic pathologic processes at the joint. (Sharma L, Pai Y-C, Holtkamp K, Rymer W Z. Is knee joint proprioception worse in the arthritic knee versus the unaffected knee in unilateral knee osteoarthritis? *Arthritis & Rheumatism.* 1997; 40:1518–1525.) They concluded that within the patients with osteoarthritis, proprioception was not worse in the arthritic knees than in the unaffected knees. These results suggest that impaired proprioception is not exclusively a local result of disease in knee osteoarthritis; rather, impaired proprioception may contribute to knee osteoarthritis.

LPS activity is measured in order to determine if a person is capable of accurately placing a limb in key positions during functional movements. Clinical measurement of proprioception is currently, in the prior art, determined by two methods: 1) single joint position placement and/or 2) mirroring. In the former, the therapist places a limb in either flexion or extension and the patient verbally indicates the position of his/her limb or duplicates the position with the contralateral limb. In the latter, the patient mimics the movement of the therapist and attempts to mirror that same movement with the contralateral limb. Also, movement detection is tested by slowly moving the limb until the person indicates a sense the limb is moving. These are static, single joint measurements that do not signify how proprioception effects movement—contrary to the above-cited research which indicates that limb position sense becomes more acute with active movement and with multisegmental joint movement.

As such, the techniques of the prior art do not directly test a person's ability to sense limb position during an ongoing functional movement. Likewise, the prior art does not test LPS acuity during different phases in the trajectory of the movement. It has been shown by previous researchers that proprioceptive input from peripheral receptors are activated differently during different phases of a movement cycle. Also, studies have shown that the central nervous system processes the peripheral input differently at different points in a movement trajectory. Other studies have shown that LPS is altered during movement compared with static or near static positioning tasks. Ongoing movement may alter the peripheral input so that LPS acuity is altered with movement.

OBJECTS OF THE INVENTION

The present invention is concerned with limb position sense as it pertains to locomotion, specifically, but not limited to, cyclic movement. Thus, an object of this invention is to assess or determine if limb position sense is more accurate during multijoint movement and phase transitions and to provide rationale for a clinical evaluation tool that more accurately measures limb position sense. It would be understood by those skilled in the art that one or more aspects of this invention can meet certain objectives, while one or more other aspects can meet certain other objectives. Each objective may not apply equally, in all its respects, to every aspect of this invention. As such, any one object can be viewed in the alternative with respect to any one aspect of this invention.

Related objects of the invention provide for a method and/or apparatus to test and prove two hypotheses: 1) that limb position sense will be enhanced with movement versus nonmovement conditions; and 2) that enhancement of limb position sense will be phase specific with greatest enhancement occurring at the two transition phases between flexion and extension. As demonstrated below and meeting such objects, limb position sense measurements as used in the clinic can become more valid with respect to functional movement.

It can be an object of the present invention to provide broad methodologies and/or systems and apparatus useful therewith to assess or improve position sense during repetitive movement, such position sense as it relates to the repetitive movement of a subject's arms, legs, hands or feet.

It can also be an object of the present invention to provide a clinical test or evaluation revealing impairments in the ability to sense limb position during movement, such that such results can be taken into account in evaluating a variety of locomotor tasks.

It can also be an object of the present invention to provide a general method for the determination or assessment of position sense such that the results obtained thereby can be communicated to an individual subject to improve use or perception of existing proprioceptive signals during movement.

It can also be an object to effect the methodologies of this invention through use of a system, apparatus and/or components other than those described herein, such components as would be well-known to those skilled in the art made aware of this invention, such components as could be obtained through straight-forward modifications of currently available components and/or apparatus, consistent with the broader teachings disclosed herein or otherwise in accordance with this invention.

Other objects, features, benefits and advantages of the present invention will be apparent from the following summary and detailed descriptions of various preferred embodiments, and would be readily apparent to those skilled in the art having knowledge of various limb position sensing technologies. Such objects, features, benefits and advantages will be apparent from the above as taken in conjunction with the accompanying examples, studies, data, figures and all reasonable inferences to be drawn therefrom, alone or in consideration with their departure from the prior art.

SUMMARY OF THE INVENTION

This invention is a novel application, both by way of methodology, system and apparatus, of limb position sense testing or assessment or determination. In preferred embodiments, individuals are asked to indicate, verbally, when they feel that their leg or arm, for example, has passed through a particular target point during cyclical movement. The verbal indication is recorded and the actual position of the limb, measured by an encoder or potentiometer, is compared to the expected target position. The error in judgement is used as an indicator of functional movement impairment during such tasks as walking, reaching, and standing up from a chair. Unlike the prior art, this invention measures limb position acuity and/or impaired locomotion during an ongoing movement rather than after the movement has stopped. Also, because limb position sense is thought to alter dependence on the particular phase of the movement trajectory, traditional methods are not valid indicators of how limb position sense is used during an ongoing movement task.

The method and/or apparatus of this invention enables clinicians, for the first time, to match limb position sense acuity to actual functional movements and, therefore, better to predict actual deficits in behavior. In various preferred embodiments, this invention can also be used as an intervention (e.g., "feedback") to train individuals to improve limb position sense during an ongoing movement, such intervention as can be accomplished through the provision, to a subject individual, comparative information regarding actual and selected positions.

In preferred embodiments, this invention can be practiced using a modified standard pedaling ergometer (either arm or leg). The standard ergometer can be equipped with a potentiometer or optical encoder that is placed at the center of crank rotation so as to precisely measure crank position. By way of example, a subject is given a microphone connected to a circuit that can generate voltage signals upon voice activation. The subject is instructed on the different positional targets of interest during the test. The subject is blindfolded, then asked to pedal slowly as the tester tells the individual to say a predetermined word "Bob" loudly and clearly as soon as he/she feels as if they have passed over the indicated target. The subject can repeatedly attempt to identify the target on multiple cyclic repetitions. Each time the subject indicates they have hit the target, a signal is generated that matches a particular crank position. A small processing unit can calculate the difference between the actual voice indicated position and the expected target position. Once calculated, the error measurement can be used to compare the subject's performance with normative values and also to indicate points in the movement trajectory where acuity is particularly impaired. Other apparatus/components providing similar function and effect—all of which can comprise commercially available components—would be apparent to those skilled in the art made aware of this invention.

As mentioned above, the invention may also be applied as an intervention. For example, as the person is cycling, he can be provided with corrective feedback about how close or far away from the expected target he was, by way of learning how to use existing proprioceptive signals, to detect important phases of the movement cycle. Accordingly, in certain embodiments, the system, components and/or apparatus of this invention can be employed as an "add-on" to any existing leg or arm powered ergometer, for use by neurologists, physical therapists, occupational therapists, health screeners, nurses, etc., again, as either a screening device or as an intervention to improve limb position sense during movement.

In light of the above and as provided elsewhere herein, the present invention is, in part, a method of assessing limb position sense accuracy. The method includes: (1) providing a test subject engaged in a repetitive movement having a trajectory with a plurality of positions thereon, the method including, but not limited to, movements of upper limbs, lower limbs, feet and hands, or a combination thereof, the subject having a particular body orientation and/or posture during the engaged movement; (2) selecting a position on the movement trajectory; (3) recording the actual position sensed by and indicated by the subject responsive to the selected position; and (4) comparing the indicated actual position with the selected position. In various preferred embodiments, the comparison or difference between indicated actual position and selected position can be provided as information to the subject during the engaged repetitive movement, as a feedback or intervention mechanism to improve use of existing proprioceptive signals and resulting limb position sense accuracy.

In various preferred embodiments, the engagement is repetitive lower limb movement, regardless of whether such movement is active, passive or has a load applied thereto. With respect to the latter variable, a variety of weighted loads or resistive forces can be applied against the repetitive movement and, hence, the limb engaging therein, so as to further assess position sense or a subject's acuity thereof.

In various other preferred embodiments, alone or in conjunction with any of the above, limb movement, whether upper or lower, can further include coincidental contralateral limb movement. For example, in the context of repetitive lower limb movement, both limbs can move together, whether in phase or out of phase one with one another. With respect to the former, both limbs can move along the same trajectory at the same time. Conversely, with respect to the latter, both limbs can move in the same trajectory at different times up to 180 degrees out of phase (i.e., where one leg is flexing while the other leg is extending). In such a manner, the present methodology can be used to assess the affect of one leg on the other during movement, as an influence on limb position sense and/or the accuracy thereof. In various other embodiments, it can be preferable to engage only one limb in repetitive movement so as to assess position sense without input from the contralateral limb.

Likewise, in preferred embodiments of the present methodologies, an especially useful repetitive movement is cyclic pedaling, an activity having various components which together simulate a walking movement. Inasmuch as limb position sense can vary depending upon rate or velocity of movement, such activities are preferably engaged at a constant rate. While preferred such methods and cyclic repetitive movements are described in conjunction with lower limb position sense, this invention in its broader aspects also contemplates various other embodiments corresponding to upper limb movement. Accordingly, a variety of components, apparatus and/or systems of the type described herein can be modified to accommodate such repetitive movement, simulating common human locomotion, not only with respect to upper and lower limbs, but also the extremities (hands and feet) thereof.

As such, the present invention also includes, in part, a system for assessing limb position sense accuracy and/or acuity during ongoing movement. Such a system includes: (1) a movement trajectory component; (2) a subject position indicator; and (3) a comparative measurement component. Various preferred system embodiments are described in more detail below in the context of angular motion. However, this would be apparent to those skilled in the art made aware of this invention, the present methodologies, components and/or systems can be applied with comparable benefit to various linear motions or combined angular/linear motions. As such, the associated movement trajectories include those of a subject's arms, legs, hands and/or feet, depending upon repetitive movement selected.

Nonetheless, in the preferred embodiments, for reasons described above, the repetitive movement is the angular motion of a cycling activity, as can be effected through use of a pedaling ergometer. Optionally, such a component can further include a potentiometer to measure pedal crank position along the movement trajectory. Various other embodiments of such a component can make effective use of well-known optical or visual tracking devices. Regardless, the indicator component is preferably a subject-activated physical signal. In highly preferred embodiments, such a subject position indicator is a voice-activated electrical signal, such as that available through use of a microphone, so as to avoid other limb or extremity contact and implication of associated proprioceptive factors.

Movement trajectory position and subject-indicated position data can be comparatively processed and/or evaluated to determine differences there between various such data processing components would be well-known to those skilled in the art made aware of this invention, and could be incorporated into the present apparatus and/or system in a straightforward fashion.

BRIEF DESCRIPTION OF THE DRAWINGS

FIG. 3 is a table providing target positions of the crank angle, as described herein.

FIG. 4 is a table providing intraclass correlation coefficients.

FIGS. 5 and 6 graphically illustrate analyses of variance to determine the existence of statistically significant differences between the conditions/phases indicated.

DETAILED DESCRIPTION OF PREFERRED EMBODIMENTS

Figure 1:
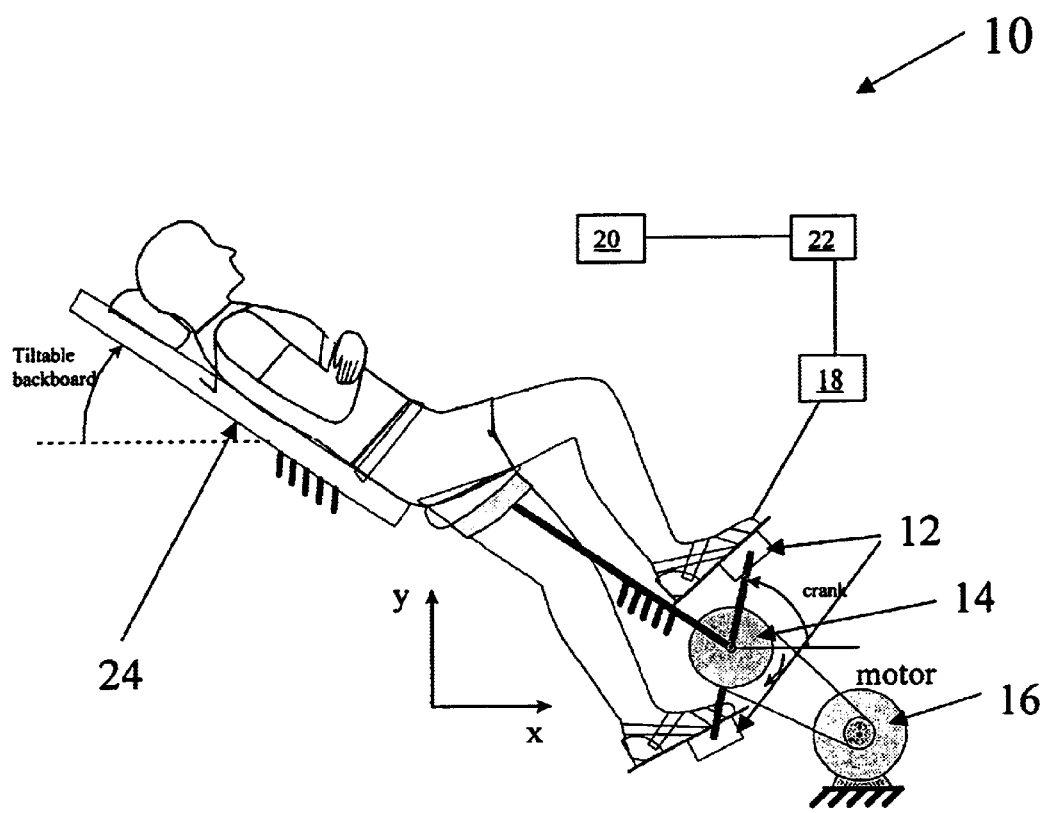
FIG. 1 is a schematic diagram showing, in accordance with this invention, a modified ergometer as a representative system for use in conjunction with the methodologies described herein.

The following describes several aspects, steps, elements and/or components of the present invention, embodiments of which would be well-known to those skilled in the art made aware of the inventive methods, system and/or apparatus otherwise provided herein. In particular, as discussed above, the present invention contemplates various apparatus and/or systems which can be used to effect the associate methodologies. With reference to FIG. 1, components of such a system/apparatus are as follows:

Movement trajectory component. Any device or instrument in accordance with the present invention that can track the trajectory or path of movement of the body (e.g., leg, arm, hand, foot, head, etc.). With respect to various embodiments, this component can be a visual tracking device (cameras and reflective markers), or a physical tracking system (body part attached to a moving element with devices that measure angular rotation or linear motion of the moving element), or any other device, component and/or system for tracking body part motion. Commercially-available ergometers are preferably employed, as discussed above, and can be equipped for movement against a motor (Kollmorgen). A crank encoder (BEI, Inc.) can also be used to gage position and speed/rate.

Position indicator. An indicator element activated when the subject believes or senses a target position reached during the ongoing movement. Such a component may be a button pushed, or a microphone spoken into, or an eye-blink indicator or any other device known in the art that detects a physical action or signal that indicates that the subject has passed through the target position.

Comparative data measurements/processing and output component. A device comparing the signal from the position indicator component and its occurrence with the point in the trajectory indicated by the movement trajectory component. A number of commercially available processing units can calculate the difference between the actual position and the sensed/indicated target position. Once calculated, the error measurement can be output to a storage device and used to compare the subject's performance with normative values and also to indicate points in the movement trajectory where acuity is particularly impaired.

Referring more specifically to FIG. 1, limb position sense system (10) is presented schematically, showing a test subject in use therewith, engaged in repetitive lower limb motion, by way of angular rotation of pedal cranks (12) of ergometer (14) against force provided by motor (16). Selected position of pedal(s) (12) is noted by encoder (18), while the corresponding position sensed by the test subject is registered by indicator (20). Both selected and actual/sensed positions are recorded by processor (22) for further use, evaluation and/or feedback to the test subject. In preferred embodiments, as shown in FIG. 1, encoder (18) can continuously measure angular crank position and speed/rate of rotation. A constant speed/rate motor assures minimalaccelerations or decelerations of pedal (12) and/or its associated crank as it passively moves the leg or as the test subject actively pedals against motor (16). As discussed above, a preferred subject position indicator (20) is a microphone that voice-activates an electric signal from indicator (20) to processor (22). As also shown in FIG. 1, the test subject is positioned on a positionable seat and surface (24) to permit a range of body orientations and loads relative thereto.

Figure 2:
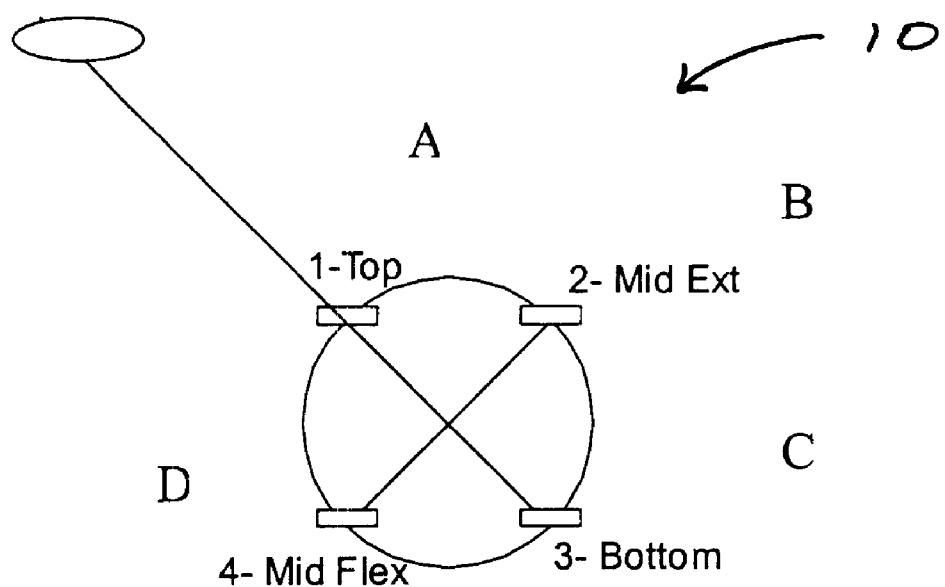
FIG. 2 is a schematic diagram showing several trajectory positions corresponding to lower limb movement using the system/ergometer of FIG. 1.

With further reference to FIG. 1, FIG. 2 is a schematic diagram showing several trajectory positions corresponding to lower limb movement. Various methods effected in accordance with the present system and/or apparatus provide for a number of selected positions along an associated movement trajectory. More specifically, with regard to angular rotation and associated limb movement, four trajectory positions are especially useful: flexion, midextension, extension and midflexion. (See FIG. 2 at positions A–D, respectively). A lessor or greater number of trajectory positions can be employed, as needed or useful for a specific movement or determination, with a corresponding number of selected position sensor components. While the schematic diagrams of FIGS. 1 and 2 are shown and described in conjunction with lower limb repetitive movement, it will be understood by those skilled in the art made aware of this invention that such a system and/or apparatus can be modified to accommodate and assess upper limb, hand and foot movement.

EXAMPLES OF THE INVENTION

The following non-limiting examples, studies and data illustrate various aspects and features relating to the systems, apparatus and/or methods of the present invention. In comparison with the prior art, the present methods, apparatus and/or systems provide results and data which are surprising, unexpected and/or contrary to the prior art. While the utility of this invention is illustrated through use of several representative devices and components, it will be understood by those skilled in the art that comparable results are obtainable with various other devices and components, as are commensurate with the broader scope of the inventive apparatus and/or methodology.

Example 1

As mentioned above, limb position sense is the ability to sense the movement and position of limbs. Clinically, limb position sense is determined in the prior art by either single joint position sense or "mirroring" of positions which are both static, single joint measurements. However, recent studies have shown that limb position sense is important during locomotor function and particularly important during certain phases of the locomotor cycle. The study of this example was undertaken, in part, to determine if limb position sense is 1) more accurate during cyclic leg movement, compared with static placement of the leg and 2) more accurate during phase transitions during cyclic pedaling (i.e., when the limb position is changing from flexion to extension and vice versa) compared with full extension or flexion.

Subjects: Sixteen healthy subjects ranging in age from 20–45 years with no known pathologies participated (mean age=26.4+/−4.69 years).

Methods: With references to FIG. 1, each subject was instructed in 3 test conditions so that their right lower extremity was either manually placed (static), moved through (passive) or self-pedaled (active) through 1 of 7 randomly selected targets with eyes open and then with eyes closed for a total of 70 trials. Subjects were asked to verbally trigger a pulse generator when they felt their foot had reached a randomly specified target region.

Analysis: The increment of error of actual position versus target position was measured between 1 of 9 possible intervals. Repeated measures analysis of variance (ANOVA) was used to determine whether statistically significant differences ($p<0.05$) existed between the static, passive and active conditions and either eyes open or eyes closed. ANOVA was also used to determine whether statistically significant differences existed between the different target regions within each condition.

Results: There was a statistically significant difference in LPS between movement versus nonmovement with the least amount of error occurring with passive movement (mean error=−0.013+/−0.700 normalized units), and active movement (mean error=−0.156+/−0.793 normalized units), and the greatest amount of error with static placement/nonmovement (mean error=0.254+/−0.628 normalized units). Furthermore, in active movement with eyes closed, intratarget differences along the movement trajectory were found with the least amount of error at extreme limb flexion (mean error=0.156+/−0.638 normalized units), and extension (mean error=−0.089+/−0.763 normalized units), and the greatest error at midextension (mean error=−0.489+/−0.661 normalized units).

Conclusion: The findings of this example support the hypotheses that limb position sense is enhanced during locomotor movement and that limb position sense is more accurate at the transition regions where limb position sense is a critical indicator of where the leg/foot is within the movement trajectory.

Relevance: Because persons with locomotor disability may be impaired by movement-dependent and/or phase-dependent limb position sense deficits, limb position sense measures will be more valid when tested within the context of locomotor movement: Accuracy is movement and phase dependent.

Example 2

Population. Experiments were performed using 16 healthy subjects ranging in age from 20–45 years and recruited from the surrounding community (mean age= 26.4+/−4.69 years). Subjects were chosen based on their health status and capabilities in pedaling a bicycle ergometer. None of the subjects were professional cyclists. The subjects reported no signs or symptoms of orthopedic impairment, cardiovascular or neurological disease. All subjects gave informed consent, and Northwestern University Institutional Review Board approved the study.

Apparatus. With reference to FIGS. 1 and 2, a standard bicycle ergometer was modified with eight sensors, which were placed along the frame of the ergometer just above the crank. These eight sensors corresponded with 30° intervals between −30° and 210°. A microphone, specially designed for this experiment, was utilized during a portion of this experiment. Whenever the percussive word "Bob" was pronounced into the microphone, an electric signal/pulse was relayed to a data file for data recording.

Protocol. The experimental protocol, conducted in a 45 minute period per subject, consisted of light pedaling with the subject seated on the ergometer with body/trunk orientation of 90° with respect to horizontal and feet firmly attached on the pedal surfaces with a strap around the forefoot. Prior to each trials, standard instructions were provided to each subject. Subjects were instructed to cross their arms over their chest once pedaling began. Subjects were informed that both legs would be moving in a cyclical motion but data would only be collected from movement of the right leg. Subjects were oriented to the target positions of the crank angle (FIG. 3). For clarity, these target positions were also illustrated on a poster. The subject held this poster in the right hand during an initial static condition. The subject was asked to warm-up for five minutes to further orient to the ergometer and protocol. The seven positions were randomized based on a table of 1000 randomized digits.

The subject right limb was either manually placed by the examiner (static condition), manually moved (passive) or self pedaled (active movement) through one of seven randomly selected targets with eyes open and then with eyes closed for a total of 70 trials. The increment of error of actual limb position versus target position was measured based on discrete 30° increments from 0° to 180°, 0° of the crank cycle was referenced relative to the seat tube. Once a steady cadence was achieved either manually by the examiner or actively by the subject, encoder data were collected and stored at 1000 samples/s.

For nonmovement or static condition, the subject was asked to maintain both legs relaxed and limp. The examiner placed the subject's legs via the right crank arm to one of seven randomly chosen positions and asked the subject "where are you now?" The examiner then rotated the right crank arm three times before placing it at another of the seven randomly chosen positions, again asking "where are you now?" and continued in this manner until all seven positions were covered each three times, first with eyes open and then with eyes blindfolded for a total of 42 trials.

For movement, passive and active conditions, subjects were oriented to the specially designed microphone, which was held in one hand by the subject and kept close to the mouth for vocal clarity. The subject said "Bob" into the specially designed microphone to indicate when he/she sensed his/her right lower extremity moving through the randomly selected target position along the movement trajectory. In passive movement, the examiner manually moved the subject's relaxed, limp right leg via the crank arm to the beat of a metronome; in active movement, the subject pedaled at the same speed or rate attained during the passive condition without assistance from the examiner. The examiner and subject proceeded as such until all seven positions were covered, first with eyes open and then with eyes blindfolded for a total of 28 trials.

Data analysis. The increment of error of actual limb position versus target position (the instant the subject verbalizes target position) was computed from the eight position sensors and translated to program LabView 5.0. For example, if the subject indicates position by saying "Bob" into the microphone at target position two after a request to indicate target position three, the subject has pedaled one interval over the target position, overshooting the correct target. If the subject has pedaled one interval under the target position, the subject has undershot the correct target.

Repeated measures analysis of variance (ANOVA) was used to determine whether statistically significant differences ($p<0.05$) existed between the conditions of movement and nonmovement and either eyes open or eyes blindfolded. ANOVA was also used to determine whether statistically significant differences existed between the different phases of movement.

Results. Reliability coefficients for each condition were very high and demonstrated the high reproducibility of error within each subject (FIG. 4). The ICC (1,1) ranged from 0.86 for the passive condition with eyes open measure to 0.98 for the active condition with eyes open measure. Analysis using ANOVA demonstrated significant differences between the conditions of movement vs. nonmovement with eyes blindfolded with passive movement (mean error= 0.013+/--0.700 normalized units) and active movement (mean error=0.156 +/-0.793 normalized units) having the least error, and static placement (mean error=0.254+/-0.628 normalized units) the greatest error (FIG. 5). The primary error in the active and passive conditions is undershooting, whereas overshooting is the primary error associated with static placement. In active movement, intraphase differences were found with the least error at target positions of extreme flexion (mean error=0.156 +/-0.683 normalized units) and extension (mean error=0.089+/--0.763 normalized units) and the greatest error at midextension (mean error=0.489+/-0.661 normalized units) (FIG. 6).

Discussion regarding study and illustrating examples. Less error occurred during movement versus nonmovement, which correlates with the first hypothesis that limb position sense will be enhanced with movement versus nonmovement conditions. The limb tested and the equipment used illustrate several distinctions over the prior art. This study tested limb position sense of the right lower extremity using a modified ergometer whereas Grandevia and Burke, for instance, tested proprioceptors innervating the human hand during active and passive movement via microneurography. Further, the latter prior art study was confined to one joint. Although microneurography permits recording during a wide range of forces and movements it does not allow the freedom to record in walking human subjects. An ergometer modified and used as described herein is an ideal assessment tool because pedaling demands multisegmental coordination of bilateral, reciprocal, symmetrical lower extremity movements, which more aptly resembles walking. Additionally, the ergometer is safe, accessible to patients with a range of ambulatory function, and is commonly used in rehabilitation.

Within active movement, intraphase differences occur with the least error at the transition phases and the greatest error at midstroke. This result correlates with the second hypothesis that enhancement of limb position sense will be phase specific with greatest enhancement occurring at the two transition phases between flexion and extension.

The right lower extremity was studied in this example because the majority of subjects were right hand dominant. An attempt was made to avoid all proprioceptive cues by instructing subjects to cross their arms over their chest so as to avoid arm contact with their lower extremities and by utilizing a blindfold for each condition. A limit to such efforts, however, is the potential for proprioceptive feedback from the contralateral limb. Second, although instructed repeatedly to relax their right lower extremity, some subjects may not have completely relaxed their right lower extremity thereby making the passive condition more like active assist. Indeed, the results show that there was no significant difference between active and passive conditions of movement. Third, detailed standard instructions were provided to each subject and allowed adequate time for each subject to orient to the ergometer and protocol. It was desired that each subject be proficient in the task at the start of the experiment. However, despite these efforts of maximizing our subject's learning, some of the subjects performed less than average, possibly adding a confounding factor to the results. Fourth, for the purpose of this study, 30° increments were chosen to capture several intervals around the two transition phases and midextension. Choice in sensor interval proved effective, although comparable results may be obtained with sensors of either lesser or greater intervals. The results of this study provide good evidence of the role limb position sense plays in movement and the need by practicing physical therapists and physical therapy educators to consider limb position sense and its impact on movement, specifically locomotion.

During a cyclic locomotor task, limb position sense was enhanced with movement and within movement condition, and limb position sense is more accurate at transition regions and less accurate at midextension. Because limb position sense is improved during movement and at transition regions of cyclic movement, the present invention and illustrative examples indicate that future clinical measures may reveal impairments in the ability to sense limb position sense during locomotor tasks, such as walking. Clear differences exist between movement versus nonmovement and phase transitions on limb position sense. Clinicians will want to take this into account when evaluating limb position sense, especially as it impacts locomotion. Future studies are already underway at Northwestern's Department of Physical Therapy and Human Movement Sciences.

While the principles of this invention have been described in connection with specific embodiments, it should be understood clearly that these descriptions are provided only by way of example and are not intended to limit, in any way, the scope of this invention. For instance, while the present invention has been described in connection with cyclic movement, angular rotation and associated systems/apparatus, it will be understood by those skilled in the art made aware of this invention that various linear movements and associated motions can be determined or assessed, consistent with the broader aspects of this invention. Other advantages and features will become apparent from the claims provided hereafter, with the scope of those claims determined by the reasonable equivalents, as would be understood by those skilled in the art.

What is claimed:

1. A method of assessing limb position sense accuracy, said method comprising:
   providing a test subject engaged in repetitive movement, said movement having a trajectory comprising a plurality of positions thereon, said movement selected from the group consisting of upper limb, lower limb, foot and hand movements and a combination of said movements, said subject having a body orientation and posture during said engagement;
   selecting one said position on said trajectory;
   recording said subject indicated actual position sensed by said subject responsive to said selected position; and
   comparing said indicated actual position with said selected position.

2. The method of claim 1 wherein said subject is provided information comparing said actual and selected positions during said movement.

3. The method of claim 1 wherein said engagement is repetitive lower limb movement.

4. The method of claim 3 wherein said engagement is selected from the group consisting of passive movement and active movement.

5. The method of claim 4 wherein said movement has a load applied thereto.

6. The method of claim 4 wherein said lower limb movement further includes contralateral limb movement.

7. The method of claim 6 wherein each said limb movement has substantially the same trajectory, each said limb at a position thereon.

8. The method of claim 4 wherein said movement comprises cyclic pedaling.

9. The method of claim 8 wherein said pedaling is at a constant rate.

10. The method of claim 8 wherein said trajectory positions are selected from the group consisting of limb flexion, limb extension, transition positions between said flexion and extension positions and combinations of said positions.

11. The method of claim 10 wherein said comparison further includes analysis to determine statistical significance.

12. The method of claim 1 wherein said engagement is repetitive upper limb movement.

13. A method of improving lower limb position sense acuity, said method comprising:
- engaging a test subject in repetitive lower limb movement, said movement having a trajectory comprising a plurality of positions thereon;
- selecting one said position on said trajectory;
- recording said subject indicated actual position sensed by said subject responsive to said selected position;
- comparing said indicated actual position with said selected position; and
- providing said subject information comparing said actual and selected positions during said movement.

14. The method of claim 13 wherein said movement is at a constant rate.

15. The method of claim 13 wherein said repetitive movement comprises cyclic pedaling.

16. The method of claim 15 wherein said pedaling is at a constant rate.

17. The method of claim 15 wherein said trajectory positions are selected from the group consisting of limb flexion, limb extension, transition positions between said flexion and extension positions and combinations of said positions.

18. A system for assessing subject limb position sense acuity during on-going movement, said system comprising a movement trajectory component, a subject position indicator, and a comparative measurement component.

19. The system of claim 18 wherein said movement trajectory component measures movement selected from the group consisting of angular rotation, linear motion and combinations of said motions, said motions of at least one of the arms, legs, hands and feet of a subject.

20. The system of claim 19 wherein said movement is angular rotation and said component is a pedaling ergometer.

21. The system of claim 20 wherein said ergometer further includes a potentiometer to measure crank position.

22. The system of claim 18 wherein said indicator is a subject activated physical signal.

23. The method of claim 22 wherein said subject position indicator is a voice activated electrical signal.

24. The system of claim 22 wherein said measurement component processes data comparing movement trajectory and subject position on said trajectory.

25. The system of claim 24 wherein said trajectory component comprises a pedaling ergometer with a potentiometer and said subject position indicator is a voice activated electrical signal, and said measurement component compares ergometer crank position with said subject position signal to determine error measurements.

26. The system of claim 25 wherein said measurement component compares subject measurements with normative values.

27. A method of using the system of claim 18 to assess lower limb position sense acuity during movement, said method comprising:
- providing an assessment system comprising a movement trajectory component, a subject position indicator, and a comparative measurement component;
- engaging a test subject in repetitive lower limb movement, said movement having a trajectory comprising a plurality of positions thereon, said engagement with said assessment system;
- selecting one said position on said trajectory;
- recording said subject indicated actual position sensed by said subject responsive to said selected position; and
- comparing said indicated actual position with said selected position.

28. The method of claim 27 wherein said engagement is selected from the group consisting of passive movement and active movement.

29. The method of claim 28 wherein said repetitive movement has a load applied thereto.

30. The method of claim 27 wherein said lower limb movement further includes contralateral limb movement.

31. The method of claim 30 wherein each said limb movement has substantially the same trajectory, each said limb at a position thereon.

32. The method of claim 27 wherein said repetitive movement comprises cyclic pedaling and said movement trajectory component is a pedaling ergometer.

33. The method of claim 27 wherein said subject is provided information comparing said actual and selected positions during said movement.

* * * * *

UNITED STATES PATENT AND TRADEMARK OFFICE
CERTIFICATE OF CORRECTION

PATENT NO. : 6,692,449 B1
DATED : February 17, 2004
INVENTOR(S) : David A. Brown It is certified that error appears in the above-identified patent and that said Letters Patent is hereby corrected as shown below:

Column 7,
Line 20, "Movement trajectory component." should be -- Movement trajectory component. --
Line 35, "Position indicator." should read -- Position indicator. --
Line 42, "Comparative data measurements/processing and output component." should be -- Comparative data measurements/processing and output component. --

Column 11,
Line 6, "+/—.700" should be -- +/- -.700 --
Line 7, "=0.156" should be -- = -.156 --
Line 15, "0.089 +/—0.763" should be -- -.089 +/- -.763 --
Line 16, "0.489" should be -- -.489 --

Signed and Sealed this

Fifteenth Day of February, 2005

JON W. DUDAS
*Director of the United States Patent and Trademark Office*